(12) United States Patent
Orr et al.

(10) Patent No.: US 11,986,592 B2
(45) Date of Patent: May 21, 2024

(54) ELECTRONIC FIREBREAK SYSTEMS AND METHODS FOR USE WITH OXYGEN DELIVERY DEVICE

(71) Applicant: Dynasthetics, LLC, Salt Lake City, UT (US)

(72) Inventors: Joseph Orr, Park City, UT (US); Kyle M. Burk, Farmington, UT (US)

(73) Assignee: Dynasthetics, LLC, Salt Lake City, UT (US)

( * ) Notice: Subject to any disclaimer, the term of this patent is extended or adjusted under 35 U.S.C. 154(b) by 477 days.

(21) Appl. No.: 17/320,536

(22) Filed: May 14, 2021

(65) Prior Publication Data

US 2022/0362495 A1  Nov. 17, 2022

(51) Int. Cl.
*A61M 16/00* (2006.01)
*A61M 16/06* (2006.01)
(Continued)

(52) U.S. Cl.
CPC ...... *A61M 16/0087* (2013.01); *A61M 16/024* (2017.08); *A61M 16/06* (2013.01);
(Continued)

(58) Field of Classification Search
CPC .............. A61M 16/00; A61M 16/0051; A61M 16/0087; A61M 16/022; A61M 16/024; A61M 16/06; A61M 16/0672; A61M 16/0816; A61M 16/0875; A61M 16/1005; A61M 16/101; A61M 16/1015;
(Continued)

(56) References Cited

U.S. PATENT DOCUMENTS 4,203,434 A * 5/1980 Brooks ............. A61M 16/0051
                                                        128/205.24
4,306,743 A  12/1981 Hinshaw et al.
(Continued)

FOREIGN PATENT DOCUMENTS

EP     1731188        12/2006
JP     2007303480      6/2009
(Continued)

OTHER PUBLICATIONS

Ballester E, Badia JR, Hernandez L, Farre R, Navajas D, Montserrat JM. "Nasal prongs in the detection of sleep-related disordered breathing in the sleep apnoea/hypopnoea syndrome," EurRespir J. Apr. 1998;11(4):880-3.
(Continued)

*Primary Examiner* — Joseph D. Boecker
(74) *Attorney, Agent, or Firm* — Dentons Durham Jones Pinegar; Sarah W. Matthews; Lilly Godfrey (57) ABSTRACT

A system and method for reducing the risk of fire in an oxygen delivery system. The system may include an oxygen delivery device with a controller in communication with a flow control valve to control a flow of oxygen through a tubing from an oxygen source to a patient interface. The controller may be programmed to close the flow control valve for a predetermined time period at a predetermined time interval to cause a periodic oxygen pause, the periodic oxygen pause to remove oxygen that may serve as an oxidizer when a fire is present inside at least one of the patient interface and the tubing.

21 Claims, 5 Drawing Sheets

(51) Int. Cl.
| | |
|---|---|
| *A61M 16/08* | (2006.01) |
| *A61M 16/10* | (2006.01) |
| *A61M 16/20* | (2006.01) |
| *A62C 2/04* | (2006.01) |
| *A62C 3/00* | (2006.01) |
| *A61M 11/00* | (2006.01) |

(52) U.S. Cl.
CPC .... *A61M 16/0672* (2014.02); *A61M 16/0816* (2013.01); *A61M 16/1005* (2014.02); *A61M 16/202* (2014.02); *A62C 2/04* (2013.01); *A62C 3/00* (2013.01); *A61M 11/00* (2013.01); *A61M 16/0875* (2013.01); *A61M 16/204* (2014.02); *A61M 2205/3334* (2013.01)

(58) Field of Classification Search
CPC ........ A61M 16/202; A61M 2016/1025; A61M 2205/3334; A62C 2/04; A62C 3/00
See application file for complete search history.

(56) References Cited

U.S. PATENT DOCUMENTS

| | | |
|---|---|---|
| 4,686,975 A | 8/1987 | Naimon et al. |
| 4,938,212 A | 7/1990 | Snook et al. |
| 5,038,771 A | 8/1991 | Dietz |
| 5,503,146 A | 4/1996 | Froehlich et al. |
| 5,551,419 A | 9/1996 | Froehlich et al. |
| 5,626,131 A | 5/1997 | Chua et al. |
| 5,865,174 A | 2/1999 | Kloeppel |
| 6,126,610 A | 10/2000 | Rich et al. |
| 6,544,192 B2 | 4/2003 | Starr |
| 6,655,383 B1 | 12/2003 | Lundberg |
| 6,938,619 B1 | 9/2005 | Hickle |
| 7,007,692 B2 | 3/2006 | Aylsworth et al. |
| 7,013,898 B2 | 3/2006 | Rashad et al. |
| 7,066,180 B2 | 6/2006 | Aylsworth et al. |
| 7,086,422 B2 | 8/2006 | Huber et al. |
| 7,115,097 B2 | 10/2006 | Johnson |
| 7,152,604 B2 | 12/2006 | Hickle |
| 7,213,594 B2 | 5/2007 | Aylsworth |
| 7,668,579 B2 | 2/2010 | Lynn |
| 7,762,253 B2 | 7/2010 | Acker et al. |
| 8,475,369 B2 | 7/2013 | Boatner et al. |
| 9,295,797 B2 | 3/2016 | Shissler et al. |
| 10,143,820 B2 | 12/2018 | Orr |
| 2002/0096174 A1 | 7/2002 | Hill et al. |
| 2002/0124845 A1 | 9/2002 | Lauer |
| 2002/0195105 A1 | 12/2002 | Blue et al. |
| 2005/0184264 A1 | 8/2005 | Tesluk et al. |
| 2005/0274381 A1* | 12/2005 | Deane ................ A61M 16/10 128/204.23 |
| 2006/0118112 A1 | 6/2006 | Cattano et al. |
| 2007/0144519 A1 | 6/2007 | Henry et al. |
| 2008/0072902 A1 | 3/2008 | Setzer et al. |
| 2009/0199855 A1 | 8/2009 | Davenport |
| 2009/0299158 A1 | 12/2009 | Boatner et al. |
| 2010/0292544 A1 | 11/2010 | Sherman et al. |
| 2011/0201956 A1 | 8/2011 | Alferness et al. |
| 2012/0055478 A1 | 3/2012 | Wilkinson |
| 2012/0118291 A1 | 5/2012 | Brodkin et al. |
| 2012/0203127 A1 | 8/2012 | Hadas |
| 2013/0152933 A1 | 6/2013 | Lischer et al. |
| 2013/0239960 A1 | 9/2013 | Bertinetti et al. |
| 2013/0317765 A1 | 11/2013 | Rao et al. |
| 2014/0116433 A1 | 5/2014 | Ghalib |
| 2014/0330155 A1 | 11/2014 | Brewer et al. |
| 2014/0360497 A1 | 12/2014 | Jafari et al. |
| 2015/0306332 A1 | 10/2015 | Bafile et al. |
| 2016/0166796 A1* | 6/2016 | Orr ................ A61M 16/0051 128/202.22 |
| 2018/0085544 A1 | 3/2018 | Holyoake et al. |

FOREIGN PATENT DOCUMENTS

| | | |
|---|---|---|
| WO | 9936118 A1 | 7/1999 |
| WO | 0118500 A1 | 3/2001 |
| WO | 2012098305 A1 | 7/2012 |
| WO | 2014106696 A1 | 7/2014 |
| WO | 2014164813 | 10/2014 |
| WO | 2016094657 A1 | 6/2016 |
| WO | 2016159787 A1 | 10/2016 |

OTHER PUBLICATIONS

Extended European Search Report dated Dec. 22, 2020 from related European application EP 20 18 8280.
Farre R, Rigau J, Montserrat JM, Ballester E, Navajas D. "Relevance of linearizing nasal prongs for assessing hypopneas and flow limitation during sleep", Am J RespirCrit Care Med. Feb. 2001;163(2):494-7.
Guyatt AR, Parker SP, McBride MJ. "Measurement of Human Nasal Ventilation Using an Oxygen Cannula as a Pilot Tube," Am J Respir. Crit Care Med. Aug. 1, 2002;166(3):386-91.
Heitman SJ, Atkar RS, Hajduk EA, Wanner RA, Flemons WW, "Validation of Nasal Pressure for the Identification of Apneas/Hypopneas during Sleep," Am Rev Respir Dis. Sep. 1982;126(3):434-8.
International Preliminary Report on Patentability, and Written Opinion of hte International Searching Authority from related application PCT/US2015/065010 dated Jun. 13, 2017.
International Preliminary Report on Patentability, and Written Opinion of the International Searching Authority from related application PCT/US2015/064998 dated Jun. 22, 2017.
International Search Report and Written Opinion of the International Searching Authority from related application PCT/ US2-15/065010 dated Mar. 7, 2016.
International Search Report and Written Opinion of the International Searching Authority from related PCT application No. PCT/US2015/064998, dated Mar. 17, 2016.
International Search Report of PCT/ FR2013/052506, dated Jan. 22, 2014.
Kohler M, Thurnheer R, Bloch KE, Side-selective, unobtrusive monitoring of nasal airflow and conductance,: J ApplPhysiol (1985). Dec. 2006; 101(6): 1760-5. Epub Jul. 13, 2006.
Hayes-Bradley, Clare, et al., "Efficacy of Nasal Cannula Oxygen as a Preoxygenation", vol. 68, Issue 2, Aug. 2016, pp. 174-180.
Montserrat JM, Farre R., "Breathing flow disturbances during sleep: can they be accurately assessed by nasal prongs?" Am J RespirCrit Med. Aug. 1, 2002;166(3):259-60.
Office Action Communication from European Patent Office in related European app. No. 15 823 860.0-1113, dated Nov. 6, 2018.
Thurnheer R, Xie X, Bloch KE, "Accuracy of nasal cannula pressure recordings for assessment of ventilation during sleep," Am J RespirCrit Care Med. Nov. 15, 2001;164(10 Pt 1):1914-9.

* cited by examiner

ELECTRONIC FIREBREAK SYSTEMS AND METHODS FOR USE WITH OXYGEN DELIVERY DEVICE

TECHNICAL FIELD

The present disclosure relates generally to a system and method to reduce the risk of fire in an oxygen delivery system. More specifically, the present disclosure relates to a method and apparatus for providing periodic oxygen pauses in oxygen delivery to reduce the risk of fire and/or extinguish a fire within the oxygen delivery system.

BACKGROUND

Oxygen is often supplied to patients during medical procedures. Known methods for regulating oxygen supply may provide increased benefits for patient safety. Such systems are disclosed, for example, in U.S. Pat. Nos. 10,159,815 and 10,143,820, which are incorporated herein in their entireties.

Administering oxygen is a therapy frequently given to patients who have difficulty breathing or who are at risk of respiratory compromise. The pure oxygen is administered through a nasal cannula, mask, oxygen tubing or other accessories. The nasal cannula, or mask, and oxygen tubing are typically made of polymeric materials (usually softened PVC) which provide flexible tubing. Although these polymeric materials are typically not flammable in room air (21% oxygen) they are highly flammable in the presence of pure oxygen. If an ignition source is present nearby while the oxygen is flowing through the flammable tubing, a fire will likely ignite and propagate up the tubing toward the oxygen source.

When oxygen is given to patients at home, oxygen fires can ignite due to patient smoking, cooking or other activities where flame or excessive heat is possible. The flame may be fueled by petroleum-based lotions on the skin. Once ignited, the fire can reach other flammable items nearby such as bed coverings and chair cushions. In the operating room, fires most often occur around the head and neck where oxygen is being administered to the patient. The ignition source for operating room fires is typically electrocautery or electrosurgical devices and additional fuels for the fire are alcohol based surgical preparation solutions and drapes which are flammable. In either setting, once the oxygen tubing has been ignited, the fire is difficult to extinguish and burns very hot while oxygen is flowing.

When the oxygen tube has been ignited, the fire propagates up the tubing, burning the inner layer of the tubing toward the oxygen source. Should the fire reach the oxygen source, the results could be catastrophic. To limit the damage caused by these fires, regulating authorities and patient safety advocates recommend placing firebreak devices in the oxygen flow path between the oxygen source and the patient.

A typical oxygen firebreak includes a thermal fuse placed in the oxygen flow path (i.e., between the oxygen tubing and the nasal cannula or mask) and is designed to stop the flow of oxygen when exposed to high heat. Physical firebreak devices are heat-operated and they close to block oxygen flow once they are exposed to high temperatures. Stopping the flow of oxygen subsequently extinguishes the fire because it removes the oxidizer feeding the fire. Ideally the firebreak device is placed between the oxygen hose and the nasal cannula or mask to stop the flow of oxygen before the fire reaches the oxygen source. The operating assumption of a firebreak device is that after the flow of oxygen is discontinued, the oxygen concentration of the surrounding gas will return to that of room air (21%) and the fire will extinguish. To limit fire propagation in the case of an oxygen fire, the firebreak should be placed as near the patient as possible between the oxygen hose and the nasal cannula or mask.

However, physical firebreak devices require installation and are only useful if the user is diligent in using them. Some medical devices, including oxygen concentrators, include an integral physical oxygen firebreak to stop the flow of oxygen so that the oxygen fire does not reach and burn the oxygen generating equipment. Another method for preventing the fire from reaching the oxygen source is to place an extended section of non-flammable (metal) tubing in the oxygen flow.

Home oxygen users sometimes remove, or fail to install, the firebreak in the oxygen tubing thereby leaving the user unprotected from oxygen-accelerated fires. Another common user error is to install the physical firebreak near the oxygen source rather than near patient's face. In this situation, the fire is not stopped until the flame traverses the full length of the hose potentially igniting everything in its path.

SUMMARY OF DISCLOSURE

A method of preventing a fire in an oxygen delivery device may comprise: opening an electronic flow control valve to deliver a flow of oxygen through tubing from an oxygen source to a patient interface, the electronic flow control valve in communication with the tubing for controlling the flow of oxygen; and at a predetermined time interval, closing the electronic flow control valve to pause the flow of oxygen for a predetermined time period, the closing of the electronic flow control valve to extinguish a fire, if the fire is present inside at least one of the patient interface and the tubing.

In some configurations, the predetermined time interval is from about every 5 seconds to about every 60 seconds, and the predetermined time period is from about 0.1 seconds to 1.5 seconds.

According to another aspect, the method further comprises the step of delivering a pulse of high-flow oxygen after closing the electronic flow control valve to pause the flow of oxygen for the predetermined time period, the pulse of high-flow oxygen further extinguishing the fire in case the fire is present in at least one of the patient interface and the tubing. The pulse of high-flow oxygen may be delivered for about 100 to about 500 milliseconds, and may have a flow rate of about 15 to about 30 liters per minute.

According to another aspect, the method may further comprise the step of compensating for the closing of the electronic flow control valve to pause the flow of oxygen, the step of compensating comprising increasing the flow of oxygen when the electronic flow control valve is open. The step of compensating may further comprise the steps of: selecting a volumetric flow rate; calculating a volume of oxygen not delivered during the closing of the electronic flow control valve based on the volumetric flow rate, the predetermined time interval, and the predetermined time period; and/or increasing the flow of oxygen when the electronic flow control valve is open to deliver the volume of oxygen not delivered during the closing of the electronic flow control valve.

According to another aspect, a method of preventing a fire in an oxygen delivery device system may comprise: providing an oxygen delivery device, the oxygen delivery device comprising a controller in communication with an electronic flow control valve; delivering a flow of oxygen from a pressurized oxygen source to a patient interface through tubing, the electronic flow control valve in communication with the tubing to selectively stop the flow of oxygen through the tubing; and at a predetermined time interval, the controller closing the electronic flow control valve to pause the flow of oxygen for a predetermined time period to remove oxygen that may serve as an oxidizer to a fire inside at least one of the patient interface and tubing. The method may also include the step of delivering a pulse of high-flow oxygen after closing the electronic flow control valve to pause the flow of oxygen for the predetermined time period, the pulse of high-flow oxygen further extinguishing the fire when the fire is present in at least one of the patient interface and the tubing.

According to another aspect, a system is described to reduce a risk of fire in an oxygen delivery system, the system comprising: an oxygen delivery device, the oxygen delivery device comprising a controller and a flow control valve to control a flow of oxygen through a tubing from an oxygen source to a patient interface; and the controller in communication with the flow control valve, the controller programmed to close the flow control valve for a predetermined time period at a predetermined time interval to cause a periodic oxygen pause, the periodic oxygen pause to remove oxygen that may serve as an oxidizer a fire inside at least one of the patient interface and the tubing.

The controller may be further programmed to cause a pulse of high-flow oxygen after the periodic oxygen pause, the pulse of high-flow oxygen extinguishing the fire inside at least one of the patient interface and the tubing. In some configurations, the pulse of high-flow oxygen may be delivered for about 100 to about 500 milliseconds, and wherein the pulse of high-flow oxygen has a flow rate of about 15 to about 30 liters per minute.

According to another aspect, the controller is programmed to compensate for the periodic oxygen pause by increasing the flow of oxygen when the flow control valve is open. The controller may be programmed to compensate for the periodic oxygen pause by: calculating a volume of oxygen not delivered during the closing of the flow control valve based on a selected volumetric flow rate, the predetermined time interval, and the predetermined time period; and increasing the flow of oxygen when the flow control valve is open to deliver the volume of oxygen not delivered during the closing of the flow control valve.

The system may comprise a patient interface, and wherein the patient interface is selected from at least one of a nasal cannula, a CPAP mask, an auxiliary oxygen tube, and a drug nebulizer. The patient interface may include a connector for connecting the patient interface to the oxygen delivery control device, and wherein the oxygen delivery device comprises a receptacle for receiving the connector of the patient interface.

BRIEF DESCRIPTION OF DRAWINGS

The following drawings illustrate what are currently considered to be specific representative configurations for carrying out the invention and are not limiting as to embodiments which may be made in accordance with the present invention. The components in the drawings are not necessarily to scale relative to each other. Like reference numerals designate corresponding parts throughout the several views.

The drawings are illustrative and not limiting of the scope of the invention which is defined by the appended claims. The various elements of the invention accomplish various aspects and objects of the invention. Not every element of the invention can be clearly displayed in a single drawing, and as such not every drawing shows each element of the invention.

DETAILED DESCRIPTION

The following provides a detailed description of particular embodiments of the present invention. Reference will now be made to the drawings in which the various elements of the illustrated configurations will be given numerical designations and in which the invention will be discussed so as to enable one skilled in the art to make and use the invention. It is to be understood that the following description is only exemplary of the principles of the present invention, and should not be viewed as narrowing the scope of the claims which follow, which claims define the full scope of the invention.

It will be appreciated that various aspects discussed in one drawing may be present and/or used in conjunction with the embodiment shown in another drawing, and each element shown in multiple drawings may be discussed only once. For example, in some cases, detailed description of well-known items or repeated description of substantially the same configurations may be omitted. This facilitates the understanding of those skilled in the art by avoiding an unnecessarily redundant description. The accompanying drawings and the following description are provided in order for those skilled in the art to fully understand the present disclosure, and these are not intended to limit the scope of claims.

Those skilled in the art will be able to devise various arrangements that, although not explicitly described herein, embody the principles of the present subject matter and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

Reference in the specification to "one configuration" "one embodiment," "a configuration" or "an embodiment" means that a particular feature, structure, or characteristic described in connection with the configuration is included in at least one configuration, but is not a requirement that such feature, structure or characteristic be present in any particular configuration unless expressly set forth in the claims as being present. The appearances of the phrase "in one configuration" in various places may not necessarily limit the inclusion of a particular element of the invention to a single configuration, rather the element may be included in other or all configurations discussed herein.

Furthermore, the described features, structures, or characteristics of configurations of the invention may be combined in any suitable manner in one or more configurations.

In the following description, numerous specific details are provided, such as examples of products or manufacturing techniques that may be used, to provide a thorough understanding of configurations of the invention. One skilled in the relevant art will recognize, however, that configurations of the invention may be practiced without one or more of the specific details, or with other methods, components, materials, and so forth. In other instances, well-known structures, materials, or operations are not shown or described in detail to avoid obscuring aspects of the invention.

The present disclosure is not limited to any particular structures, process steps, or materials discussed or disclosed herein, but is extended to include equivalents thereof as would be recognized by those of ordinary skill in the relevant art. More specifically, the invention is defined by the terms set forth in the claims. Terminology contained herein is used for the purpose of describing particular aspects of the invention only and is not intended to limit the invention to the aspects or configurations shown unless expressly indicated as such. Likewise, the discussion of any particular aspect of the invention is not to be understood as a requirement that such aspect is required to be present apart from an express inclusion of the aspect in the claims.

As used in this specification and the appended claims, singular forms such as "a," "an," and "the" may include the plural unless the context clearly dictates otherwise. Thus, for example, reference to "an electronic flow control valve" may include one or more of such valves, and reference to "the controller" or "the processor" may include reference to one or more of such controllers or such processors. Those skilled in the art should be familiar with the use of controllers in processing environments generally and, more specifically, with main memory databases. Controllers as described herein may be implemented in software, firmware, hardware or some suitable combination of at least two of the three.

As used herein, the term "substantially" refers to the complete or nearly complete extent or degree of an action, characteristic, property, state, structure, item, or result to function as indicated. For example, an oxygen delivery tube that is "substantially" closed by an electronic flow control valve may be either completely closed or nearly completely closed. The use of "substantially" is equally applicable when used in a negative connotation to refer to the complete or near complete lack of an action, characteristic, property, state, structure, item, or result. As used herein the term "generally" refers to something that is more of the designated adjective than not, or the converse if used in the negative. As used herein, the term "about" is used to provide flexibility to a numerical range endpoint by providing that a given value may be "a little above" or "a little below" the endpoint while still accomplishing the function associated with the range. As used herein, a plurality of items, structural elements, compositional elements, and/or materials may be presented in a common list for convenience. However, these lists should be construed as though each member of the list is individually identified as a separate and unique member.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 5 to about 60" should be interpreted to include not only the explicitly recited values of about 1 to about 5, but also include individual values and sub-ranges within the indicated range. Thus, included in this numerical range are individual values such as 6, 7, 8, 9, etc., through 60, and sub-ranges such as from 10-20, from 30-40, and from 50-60, etc., as well as each number individually. This same principle applies to ranges reciting only one numerical value as a minimum or a maximum. Furthermore, such an interpretation should apply regardless of the breadth of the range or the characteristics being described.

It will also be appreciated by those skilled in the art that the words during, while, and when as used herein are not exact terms that mean an action takes place instantly upon an initiating action but that there may be some small but reasonable delay, such as a propagation delay, between the initial action and the reaction that is initiated by the initial action. Additionally, the word "connected" and "coupled" is used throughout for clarity of the description and can include either a direct connection or an indirect connection.

The present disclosure relates generally to a system and method for providing an electronic firebreak in an oxygen delivery system, or reducing the risk of fire in an oxygen system, by periodically stopping the flow of oxygen in an oxygen delivery system. As used herein, a firebreak is any device or method to prevent a fire from occurring, or to help extinguish a fire that has already occurred. Therefore, the steps and systems described herein may be used regardless if a fire is currently present, as they can serve to both prevent fires and extinguish fires. Additionally, as used herein to "extinguish" a fire means to either entirely put out a fire and/or to diminish a fire that is present without entirely putting the fire out. Thus, steps taken by the systems and methods described herein may serve to prevent a fire when no fire is present and/or extinguish a fire even if the fire is not entirely put out.

Figure 1:
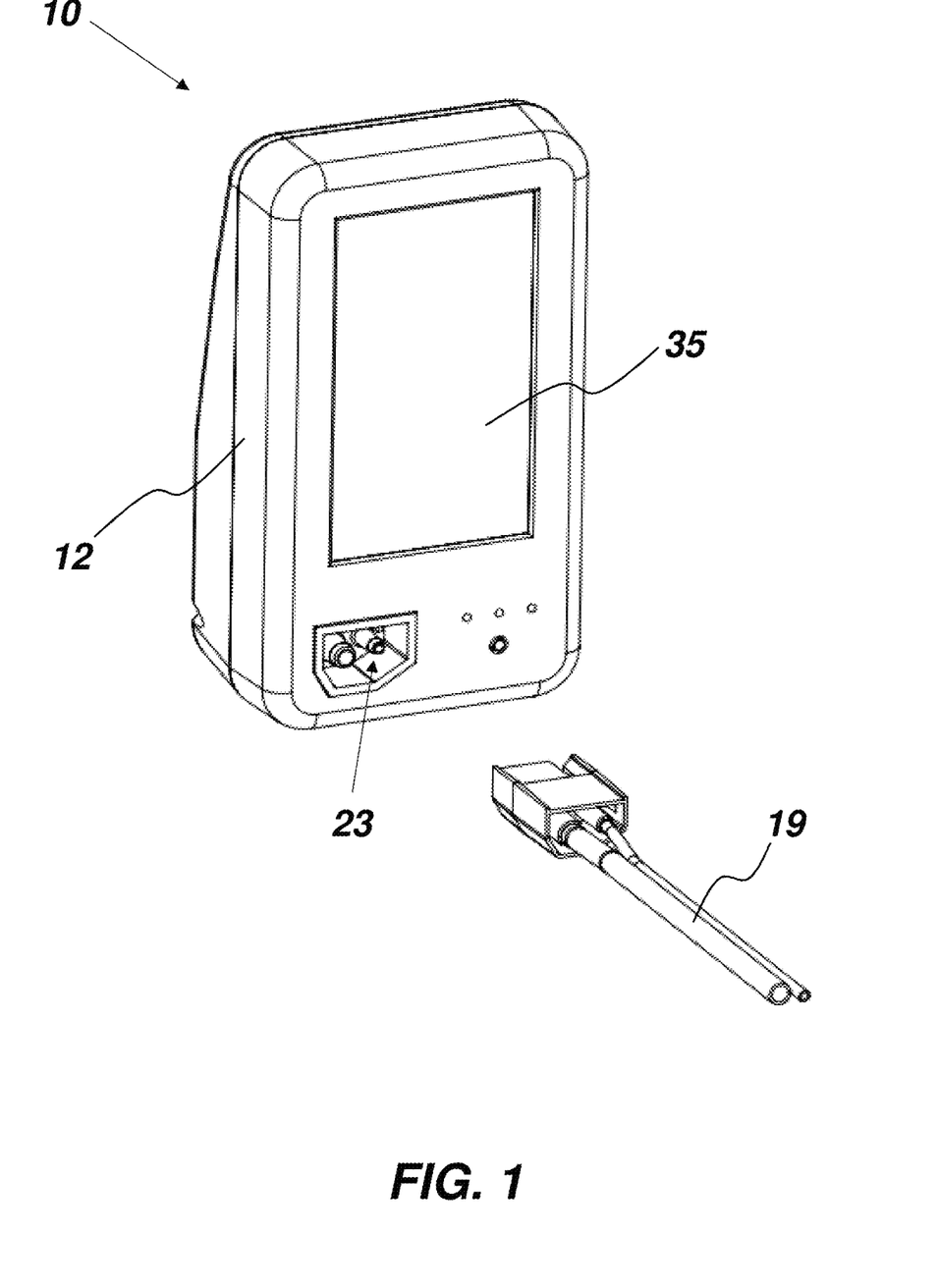
FIG. 1 is a perspective view of an exemplary system for reducing a risk of a fire in an oxygen delivery system.
Figure 2:
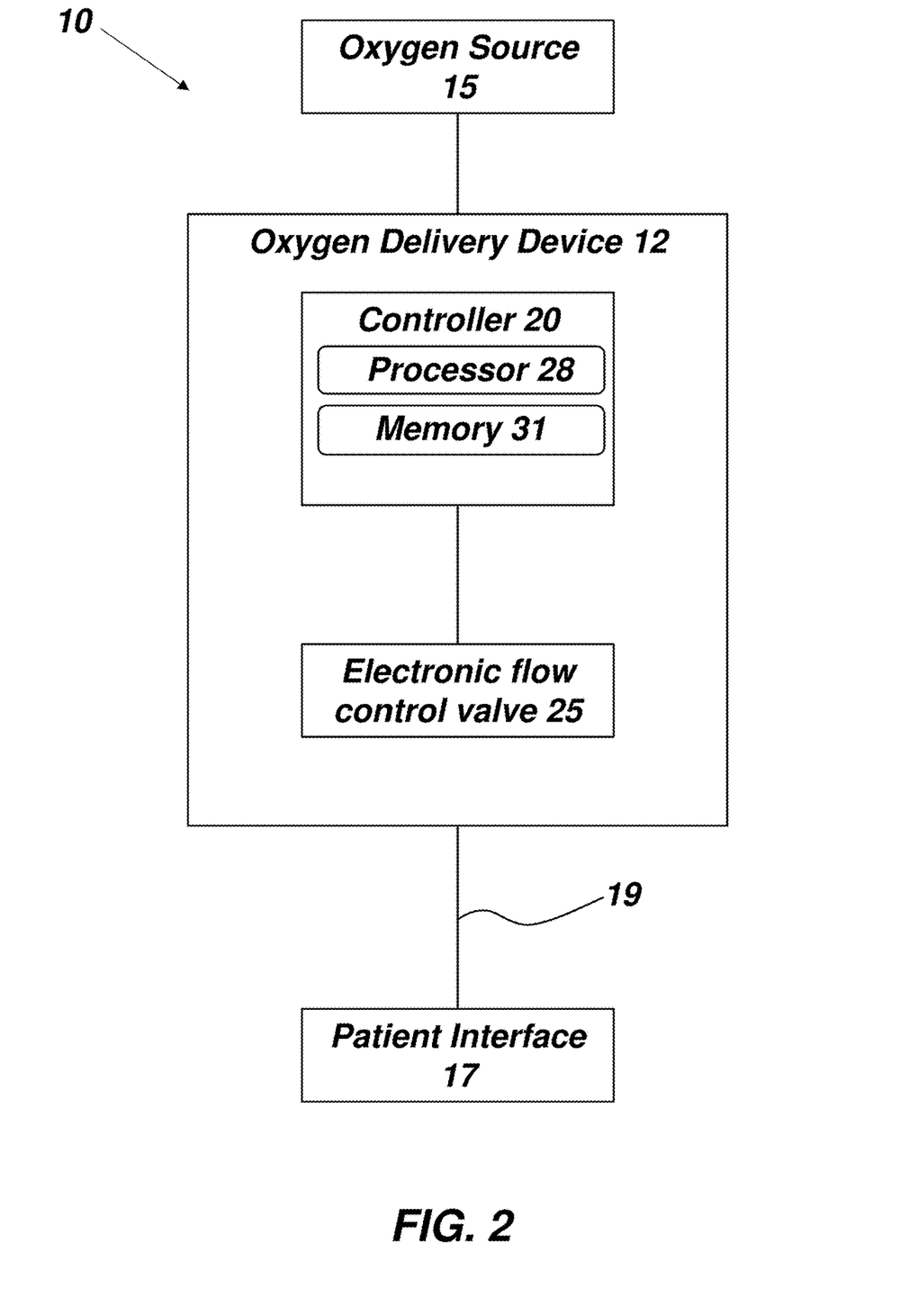
FIG. 2 is a block diagram of an exemplary system for reducing a risk of a fire in an oxygen delivery system.
Figure 3:
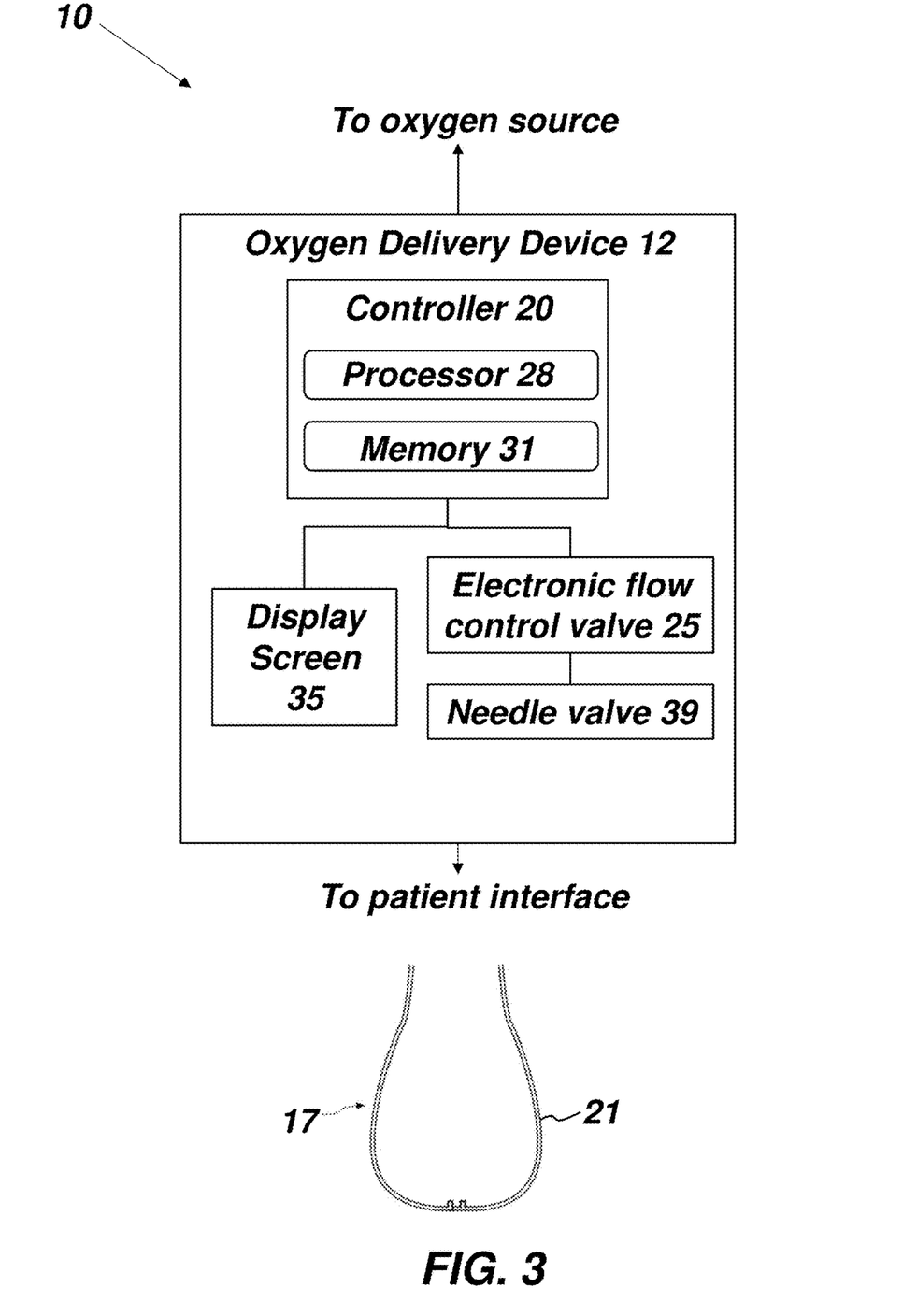
FIG. 3 is a block diagram of another exemplary system for reducing a risk of a fire in an oxygen deliver system.

FIGS. 1-3 show an exemplary systems 10 for reducing a risk of fire in an oxygen delivery system. The system 10 may generally comprise an oxygen delivery device 12 that may be used to deliver oxygen to a patient, from an oxygen source 15 to a patient interface 17. The oxygen delivery device 12 may have several possible configurations depending on the desired applications. In the exemplary configuration shown in FIG. 2, the oxygen delivery device 12 includes a controller 20 in communication with an electronic flow control valve 25.

The electronic flow control valve 25 may be provided in connection with an oxygen source 15 to enable medical personnel to select, adjust, or control the oxygen flow rate from the oxygen source 15 to the patient interface 17. The electronic flow control valve 25 may be any suitable flow control valve. For example, in some configurations, a needle valve may be used. The electronic flow control valve 25 may be a simple ON/OFF type valve that has only two positions: open and closed. In other configurations, the electronic flow control valve 25 may provide a variable flow of oxygen. In other configurations, the system may be provided with an electronic flow control valve 25 for ON/OFF capabilities, and a second control valve for controlling the flow rate (see below for additional discussion in conjunction with the exemplary configuration shown in FIG. 3).

The patient interface 17 may be a nasal cannula 21, as shown in the exemplary configuration of FIG. 3, such as a single- or double-nared nasal cannula, or it may be a mask or other suitable device. The patient interface 17 may be provided with a connection, such as tubing 19, to an oxygen source 15 in communication with the oxygen delivery device 12. The connection between the patient interface 17 and the oxygen source may be direct or indirect, such as through an oxygen delivery device 12. As used herein, a "patient interface" may include only a mask or nasal cannula, etc., or it may also be used to refer generally to the mask, nasal cannula, etc., as well as the tubing used to connect it to the oxygen source. In some configurations, the oxygen delivery device 12 may comprise a receptacle 23 (FIG. 1) for receiving a connector of a patient interface 17.

In order to reduce the risk of fire and/or extinguish a fire that is present, controller 20 may be programmed to cause the electronic flow control valve 25 to close entirely or substantially entirely for a predetermined time period at a predetermined time interval. This may serve to cut off the oxygen in the patient interface 17. By removing the oxygen that may serve as the oxidizer for a fire inside the patient interface 17, any fire present may be either significantly diminished or entirely extinguished. The controller 20 may then cause the electronic flow control valve 25 to re-open. This periodic oxygen pause may be taken at set intervals, regardless of whether a fire is present or not, and thus works to both prevent fires as well as extinguish fires that may be present.

The predetermined time interval may be any suitable interval. In some configurations, the predetermined time interval may be set by a clinician and may be unique to the particular patient and the particular environment. In other configurations, the predetermined time interval may be selected by software based on known parameters, such as the age and/or condition of the patient. In yet other configurations, a predetermined time interval may be programmed into software for the controller and be standard for all patients. The predetermined time interval need not be the same interval but may also vary, such as a continuous variance or a patterned variance, such as a 5-second time interval, followed by a periodic oxygen pause, followed by a 10-second time interval, followed by a periodic oxygen pause, etc. The predetermined time interval may be set, for example, from about every 5 seconds to about every 60 seconds. The predetermined time interval may also be set shorter or longer depending on the patient and the environmental conditions.

Similarly, the predetermined time period may be any suitable time period to allow the oxygen in the patient interface 17 to be depleted or nearly depleted. For example, the predetermined time period may be from about 0.1 seconds to about 1.5 seconds. The predetermined time period may be set by a clinician and may be unique to the particular patient and environment. In other configurations, the predetermined time period may be selected by software based on known parameters, such as the age and/or condition of the patient. In yet other configurations, the predetermined time period may be programmed into software for the controller and be standard for all patients. The predetermined time period need not be the same time period for each periodic oxygen pause. For example, the predetermined time period may vary or continuously vary from one periodic oxygen pause to the next. A short time period causing a short oxygen pause (closer to 0.1 seconds) may be followed by a longer time period causing a longer oxygen pause (closer to 1.5 seconds). A plurality of predetermined time periods for the periodic oxygen pause, either all the same, varying periodically, or continuously varying, may be possible and are contemplated herein.

With reference to the controller 20, the controller 20 may include one or more processors 28, memory 31 and programmable input/output peripherals, and the disclosed embodiments are not limited to any specific type of controller(s) or processor(s). The processor 28 may be in communication with memory 31, which may include one or more storage devices configured to store instructions used by processor to perform functions related to disclosed embodiments (such as closing and/or opening the electronic control valve 25, etc.). For example, the memory 31 may be configured with one or more software instructions, such as programs that may perform one or more operations when executed by the processor 28. The disclosed embodiments are not limited to separate programs or computers configured to perform dedicated tasks. For example, memory 31 may include a single program that performs the functions of the processor 28, or memory 31 may comprise multiple programs. Memory 31 may also store data that is used by one or more programs (such as pre-set oxygen delivery flow rates, predetermined time intervals, predetermined time periods, etc.), and/or a controller 20. In some configurations, memory 31 and associated applications may be stored within the oxygen delivery device 12, and in other configurations, memory 31 and associated applications may be stored at a remote location for storage and processing by the controller 20 and/or in the cloud, such as a network, etc.

The functions of the various elements shown in the figures, including any functional blocks labeled as "controller(s)" and/or "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), flash memory, and/or non-volatile storage. Other hardware, conventional and/or custom, may also be included within the controller 20 and/or oxygen delivery device 12.

In some configurations, the controller 20 may be programmed, through one or more processor(s) 28 and memory 31, to send a signal to the electronic flow control valve 25 to close for a predetermined time period at a predetermined time interval as described above to cut off the oxygen in the patient interface 17. By removing the oxygen that may serve as the oxidizer for a fire inside the patient interface 17, any fire present may be either significantly diminished or entirely extinguished. The controller 20 may then be programmed, through one or more processor(s) 28 and memory 31, to send a signal to cause the electronic flow control valve 25 to re-open.

In some configurations, the controller 20 may be in communication with one or more input and/or output devices. For example, the oxygen delivery device 12 may include a display screen 35 (FIGS. 1 and 3) in communication with the controller 20. The display screen may also serve as an input device, allowing a user to make selections on the display screen. A separate input device, such as a keyboard, etc., may also be used to provide input to the controller 20. An input device may allow a clinician to specifically set parameters for oxygen delivery based on the unique needs of the patient. For example, a clinician may set a specific flow rate of oxygen may be delivered to the patient. This may be delivered either by controlling the electronic flow control valve 25, or in some configurations, a separate needle valve 39 may be provided.

For example, as seen in the exemplary configuration of FIG. 3, the oxygen delivery device 12 may further comprise a needle valve 39 that may be separately controlled apart from the electronic flow control valve 25. The controller 20 may be used to control the needle valve 39 to deliver a specific flow rate of oxygen to a patient. For example, the processor 28 may set a flow rate that changes up to 100 times per second according to variables such as the desired oxygen delivery for the particular patient. The variable-type of flow control valve 39 may be, for example, those known in the art such as the EVP Series Proportional Control Valves manufactured by Clippard Instrument Laboratory, Inc. In other configurations, a separate needle valve 39 may not be provided, and the electronic flow control valve 25 may be used to deliver a specific flow rate of oxygen to a patient.

In some settings, a clinician may set a desired oxygen flow rate for a patient with the goal of delivering a specific volume of oxygen to the patient over time. Because the present system 10 periodically causes the oxygen delivery to pause for the goal of reducing fire risk, in some configurations, the system 10 may be programmed to compensate for the periodic oxygen pause. When it is desirable to achieve a specific average volumetric flow rate, the controller 20 may be programmed, through one or more processor(s) 28 and memory 31, to increase the flow rate of oxygen while oxygen is being delivers to compensate for the decrease in per minute oxygen flow caused by the periodic oxygen pauses. The flow rate of oxygen may be increased through one or more of the electronic flow control valve 25 and/or a needle valve 39.

For example, a clinician may desire an overall oxygen flow rate of 6,000 milliliters (mL) per minute. The system 10 may be provided with a pause of a predetermined time period (such as 0.25 seconds) at a predetermined time interval (such as every 15 seconds), resulting in a periodic oxygen pause 4 times per minute for a total of 1 second of oxygen pause per minute. In this scenario, the overall volume of oxygen given in one minute would be reduced by $\frac{1}{60}$th (1 second per every 60 seconds). This equates to a volumetric loss of 6,000 mL·1 s/60 s=100 mL. Due to the periodic oxygen pauses, only 5,900 mL (6,000 mL-100 mL=5,900 mL) would be delivered each minute, with 5,900 mL being delivered for 59 seconds and 0 mL delivered during the remaining second. However, the 100 mL of oxygen lost during the pause could be delivered during the other 59 seconds that oxygen flows. To achieve this, the system 10 may be programmed to instead give the full 6,000 mL during the 59 seconds of oxygen flow, which requires a flow rate of 6,000 mL/59 s*60 s=6101 mL/minute. A flow rate of 6101 mL/minute for 59 seconds and 0 mL/minute for 1 second would achieve an average volumetric flow rate of 6,000 mL/minute and fully compensate for the oxygen not delivered during the periodic oxygen pause.

In other configurations, it may not be desirable or necessary to compensate for the oxygen not delivered during the periodic oxygen pause. Thus, in some configurations, the system may not compensate for the decreased volume of oxygen due to the periodic oxygen pause.

According to another aspect, the system 10 may be programmed to further reduce the risk of fire and/or extinguish a fire that is present by optionally delivering a brief pulse of high-flow oxygen immediately following the periodic oxygen pause. In other configurations, the pulse of high-flow oxygen may not be given. In configurations where a high-flow pulse is desired, the controller 20 may be programmed, through one or more processor(s) 28 and memory 31, to increase the flow rate after the periodic oxygen pause. It is know that fire travels up the oxygen tubing more slowly when oxygen flow rate is higher. A brief pulse of high-flow oxygen may be able to blow out a small flame burning at the end of the oxygen tubing. A brief pulse of high-flow oxygen immediately following the periodic oxygen pause described above can further help extinguish a fire when a fire is present.

Where a brief pulse of high-flow oxygen is desired, the brief pulse of high-flow oxygen may be given for example, for about 100 milliseconds to about 500 milliseconds, and may have a flow from about 15 liters per minute to about 30 liters per minute. It will be appreciated that in configurations where the system does use a brief pulse of high-flow oxygen, the overall oxygen flow rate may be adjusted to compensate for the increased oxygen during the brief pulse of high-flow oxygen. In other configurations, the system may not adjust the overall oxygen flow rate based on the high-flow oxygen pulse.

Figure 4:
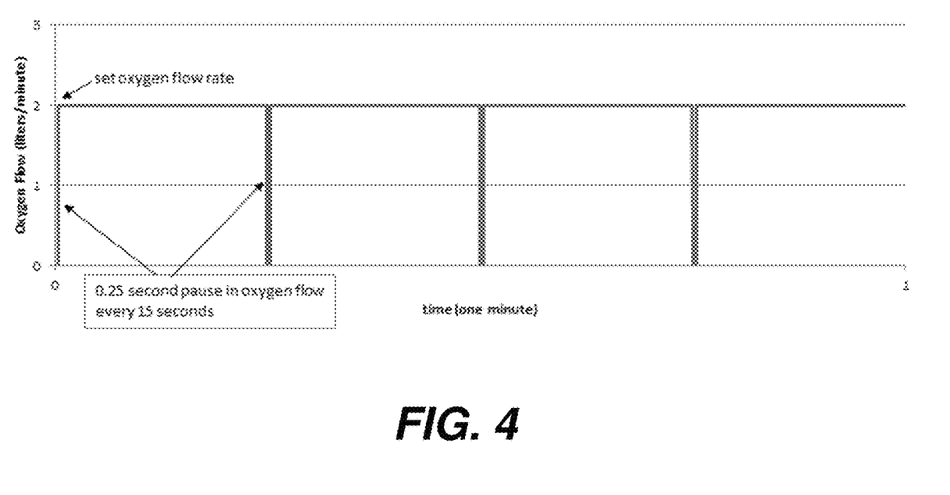
FIG. 4 is an exemplary continuous oxygen flow waveform showing a periodic oxygen pause as described herein.

FIG. 4 shows an exemplary continuous oxygen flow waveform showing an electronic firebreak as described herein, with the oxygen flow in liters/minute shown on the y-axis and the time shown on the x-axis. A flow rate of two liters per minute is shown for a one minute period. The periodic oxygen pause shown in the example in FIG. 4 is for a predetermined time period of 0.25 seconds and the predetermined time interval is once every 15 seconds. In this configuration, no compensation is shown for the oxygen not delivered during the periodic oxygen pause and no pulse of high-flow oxygen is provided. In other configurations, the system may be selected to compensate for the periodic oxygen pause and/or deliver a pulse of high-flow oxygen after the periodic oxygen pause. These settings may be either selected by a clinician based on the needs of the patient and/or the environment of the patient, or they may be pre-programmed.

Figure 5:
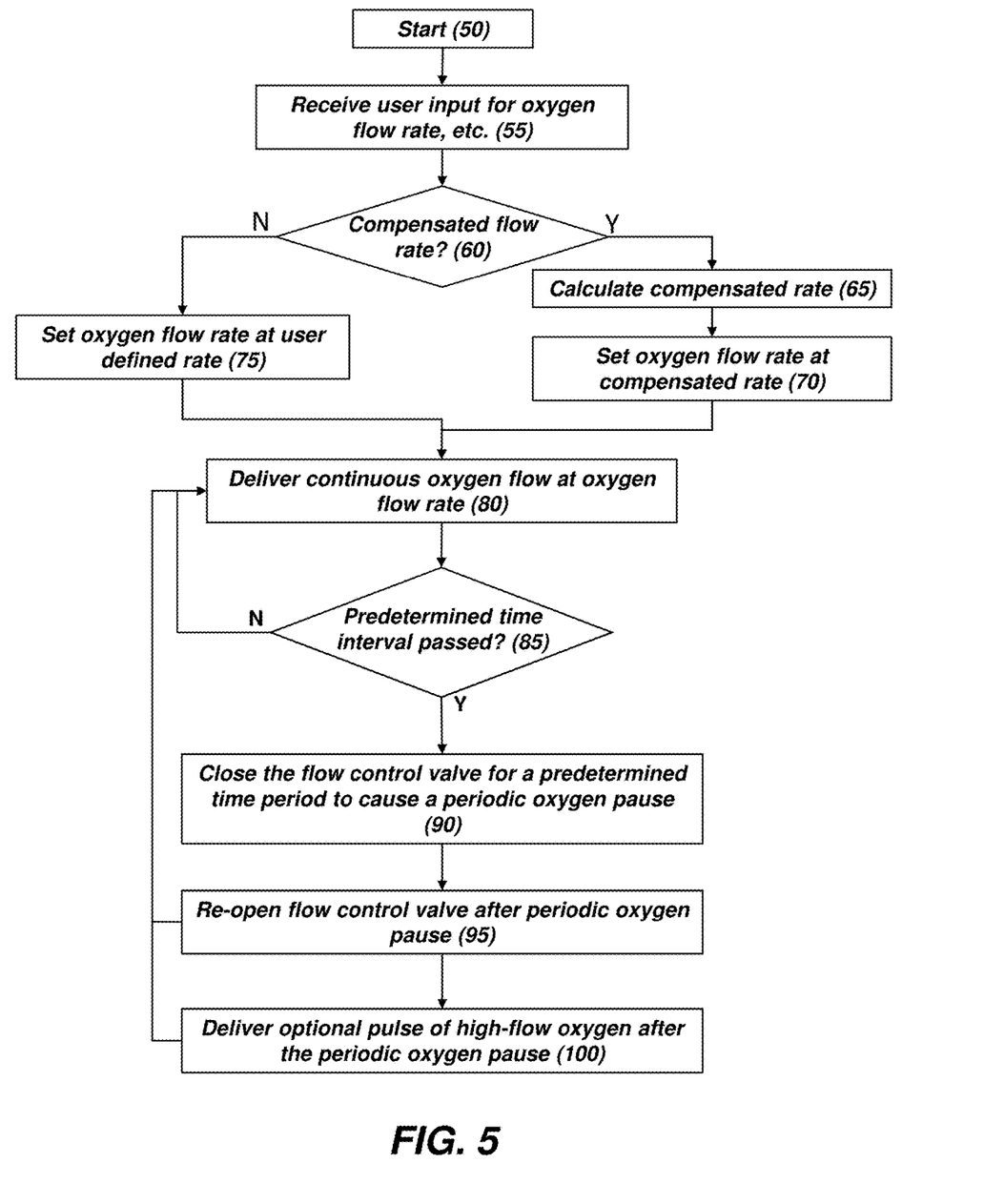
FIG. 5 is an exemplary flow diagram of steps that may be taken in one configuration of the system as described herein.

FIG. 5 shows exemplary logic that may be used by the controller 20 and/or processor(s) 28. After a start 50, a clinician may select one or more parameters for the oxygen delivery control device 12. For example, a clinician may input details regarding the particular patient, and the processor 28, based on one or more programs stored in memory 31, may select the appropriate oxygen delivery parameters for the patient, such as the oxygen flow rate, the predetermined time period for the periodic oxygen pause, and/or the predetermined time interval for the periodic oxygen pause. In other configurations, the clinician may directly select these parameters. In yet other configurations, standard parameters may be programmed into the oxygen delivery device 12 and the controller need not receive any user input.

After the controller receives user input for the oxygen flow rate, etc., (55 in FIG. 5) (or, alternatively in some configurations, user input need not be received), the system may then determine if it is desirable to deliver a compensated flow rate (60 in FIG. 5). This may be determined, for example, by input received from a clinician, by one or more programs stored in memory 31, etc. Where it is desirable to provide a compensated flow rate, the system 10 may compensate by increasing the flow of oxygen when the electronic flow control valve 25 is open. The system may calculate the compensated flow rate based on the volumetric flow rate, the predetermined time interval, and the predetermined time period (65) as described in detail above, and then set the oxygen flow rate at the compensated rate (70). When the electronic flow control valve 25 is open, the volume of oxygen not delivered during the closing of the electronic flow control valve may be compensated by the compensated rate. In configurations where no compensation is desired and/or needed, the oxygen flow rate may be set at the user defined flow rate (75) (or a system defined flow rate as described above).

The system may then proceed to deliver a continuous or nearly continuous oxygen flow at the oxygen flow rate (80), which may be a compensated rate or a uncompensated rate. The oxygen flow rate may be controlled either by use of a separate valve, such as a needle valve, or may be controlled directly by the electronic flow control valve 25. The system may proceed to deliver the continuous oxygen flow until the predetermined time interval has passed (85). When the predetermined time interval has passed, the controller 20 may then send a signal to the electronic flow control valve 25 to close the electronic flow control valve 25 for a predetermined time period to cause a periodic oxygen pause (90). After the periodic oxygen pause, the electronic flow control valve 25 may be re-opened (95). The system may then continue back to delivering the continuous oxygen flow (80), or, optionally, the system may first deliver a pulse of high-flow oxygen after the periodic oxygen pause (100) before returning to delivering the continuous oxygen flow (80).

It will be appreciated that the presently disclosed system does not require a physical device to be installed, so unlike the prior art physical firebreaks, it cannot be removed by the user. Home oxygen users sometimes remove, or fail to install, the firebreak in the oxygen tubing thereby leaving the user unprotected from oxygen accelerated fires. Another common user error is to install the physical firebreak near the oxygen source rather than near patient's face. In this situation, the fire is not stopped until the flame traverses the full length of the hose potentially igniting everything in its path. The present system cannot be removed by the user and its efficacy is not determined by its location within the plumbing of the oxygen tubing. Instead, the system 10 is always active and extinguishes the fire regardless of the position on the tubing that the fire is located.

Aspect A: A method of preventing a fire in an oxygen delivery device, the method comprising: opening an electronic flow control valve to deliver a flow of oxygen through tubing from an oxygen source to a patient interface, the electronic flow control valve in communication with the tubing for controlling the flow of oxygen; and at a predetermined time interval, closing the electronic flow control valve to pause the flow of oxygen for a predetermined time period, the closing of the electronic flow control valve to extinguish a fire, if the fire is present inside at least one of the patient interface and the tubing.

Aspect B: The method of Aspect A, wherein the predetermined time interval is from about every 5 seconds to about every 60 seconds.

Aspect C: The method of Aspects A or B, wherein the predetermined time period is from about 0.1 seconds to 1.5 seconds.

Aspect D: The method of any of Aspects A through C, wherein the method further comprises the step of delivering a pulse of high-flow oxygen after closing the electronic flow control valve to pause the flow of oxygen for the predetermined time period, the pulse of high-flow oxygen further extinguishing the fire in case the fire is present in at least one of the patient interface and the tubing.

Aspect E: The method of Aspect D, wherein the pulse of high-flow oxygen is delivered for about 100 to about 500 milliseconds, and wherein the pulse of high-flow oxygen has a flow rate of about 15 to about 30 liters per minute.

Aspect F: The method of any of Aspects A through E, wherein the method further comprises the step of compensating for the closing of the electronic flow control valve to pause the flow of oxygen, the step of compensating comprising increasing the flow of oxygen when the electronic flow control valve is open.

Aspect G: The method of Aspect F, wherein the step of compensating further comprises the steps of: selecting a volumetric flow rate; calculating a volume of oxygen not delivered during the closing of the electronic flow control valve based on the volumetric flow rate, the predetermined time interval, and the predetermined time period; and wherein the method further comprises increasing the flow of oxygen when the electronic flow control valve is open to deliver the volume of oxygen not delivered during the closing of the electronic flow control valve.

Aspect H: A method of preventing a fire in an oxygen delivery device system, the method comprising: providing an oxygen delivery device, the oxygen delivery device comprising a controller in communication with an electronic flow control valve; delivering a flow of oxygen from a pressurized oxygen source to a patient interface through tubing, the electronic flow control valve in communication with the tubing to selectively stop the flow of oxygen through the tubing; and at a predetermined time interval, the controller closing the electronic flow control valve to pause the flow of oxygen for a predetermined time period to remove oxygen that may serve as an oxidizer to a fire inside at least one of the patient interface and tubing.

Aspect I: The method of Aspect H, wherein the predetermined time interval is from about every 5 seconds to about every 60 seconds, and wherein the predetermined time period is from about 0.1 seconds to 1.5 seconds.

Aspect J: The method of Aspect H or I, wherein the method further comprises the step of delivering a pulse of high-flow oxygen after closing the electronic flow control valve to pause the flow of oxygen for the predetermined time period, the pulse of high-flow oxygen further extinguishing the fire when the fire is present in at least one of the patient interface and the tubing.

Aspect K: The method of any of aspects H through J, wherein the pulse of high-flow oxygen is delivered for about 100 to about 500 milliseconds, and wherein the pulse of high-flow oxygen has a flow rate of about 15 to about 30 liters per minute.

Aspect L: The method of any of aspects H through K, wherein the method further comprises the step of compensating for the closing of the electronic flow control valve to pause the flow of oxygen, the step of compensating comprising increasing the flow of oxygen when the electronic flow control valve is open.

Aspect M: The method of any of aspects H through L, wherein the step of compensating for the closing of the electronic flow control valve to pause the flow of oxygen further comprises the steps of: selecting a volumetric flow rate; calculating a volume of oxygen not delivered during the closing of the electronic valve based on the volumetric flow rate, the predetermined time interval, and the predetermined time period; and wherein the method further comprises increasing the flow of oxygen when the electronic flow control valve is open to deliver the volume of oxygen not delivered during the closing of the electronic flow control valve.

Aspect N: A system for reducing a risk of fire in an oxygen delivery system, the system comprising: an oxygen delivery device, the oxygen delivery device comprising a controller and a flow control valve to control a flow of oxygen through a tubing from an oxygen source to a patient interface; and the controller in communication with the flow control valve, the controller programmed to close the flow control valve for a predetermined time period at a predetermined time interval to cause a periodic oxygen pause, the periodic oxygen pause to remove oxygen that may serve as an oxidizer a fire inside at least one of the patient interface and the tubing.

Aspect O: The system for reducing the risk of fire in an oxygen delivery system of Aspect N, wherein the predetermined time interval is from about every 5 seconds to about every 30 seconds and wherein the predetermined time period is from about 0.1 seconds to 1.5 seconds.

Aspect P: The system for reducing the risk of fire in an oxygen delivery system of Aspects N or O, wherein the controller is further programmed to cause a pulse of high-flow oxygen after the periodic oxygen pause, the pulse of high-flow oxygen extinguishing the fire inside at least one of the patient interface and the tubing.

Aspect Q: The system for reducing the risk of fire in an oxygen delivery system of any of aspects N through P, wherein the controller is programmed to cause the pulse of high-flow oxygen to be delivered for about 100 to about 500 milliseconds, and wherein the pulse of high-flow oxygen has a flow rate of about 15 to about 30 liters per minute.

Aspect R: The system for reducing the risk of fire in an oxygen delivery system of any of aspects N through Q, wherein the controller is programmed to compensate for the periodic oxygen pause by increasing the flow of oxygen when the flow control valve is open.

Aspect S: The system for reducing the risk of fire in an oxygen delivery system of any of aspects N through R, wherein the controller is programmed to compensate for the periodic oxygen pause by: calculating a volume of oxygen not delivered during the closing of the flow control valve based on a selected volumetric flow rate, the predetermined time interval, and the predetermined time period; and increasing the flow of oxygen when the flow control valve is open to deliver the volume of oxygen not delivered during the closing of the flow control valve.

Aspect T: The system for reducing the risk of fire in an oxygen delivery system of any of aspects N through S, the system further comprising the patient interface, and wherein the patient interface is selected from at least one of a nasal cannula, a CPAP mask, an auxiliary oxygen tube, and a drug nebulizer.

Aspect U: The system for reducing the risk of fire in an oxygen delivery system of any of aspects N through T, wherein the patient interface includes a connector for connecting the patient interface to the oxygen delivery control device, and wherein the oxygen delivery device comprises a receptacle for receiving the connector of the patient interface.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A method of preventing a fire in an oxygen delivery system, the method comprising:
    opening an electronic flow control valve to deliver a flow of oxygen through tubing from an oxygen source to a patient interface, the electronic flow control valve in communication with the tubing for controlling the flow of oxygen; and
    at a predetermined time interval, closing the electronic flow control valve to pause the flow of oxygen for a predetermined time period, the predetermined time period being less than the predetermined time interval, the closing of the electronic flow control valve to extinguish a fire, if the fire is present inside at least one of the patient interface and the tubing.

2. The method of claim 1, wherein the predetermined time interval is from about every 5 seconds to about every 60 seconds.

3. The method of claim 1, wherein the predetermined time period is from about 0.1 seconds to 1.5 seconds.

4. The method of claim 1, wherein the method further comprises delivering a pulse of high-flow oxygen after closing the electronic flow control valve to pause the flow of oxygen for the predetermined time period, the pulse of high-flow oxygen further extinguishing the fire in case the fire is present in at least one of the patient interface and the tubing.

5. The method of claim 4, wherein the pulse of high-flow oxygen is delivered for about 100 to about 500 milliseconds, and wherein the pulse of high-flow oxygen has a flow rate of about 15 to about 30 liters per minute.

6. The method of claim 1, wherein the method further comprises compensating for the closing of the electronic flow control valve to pause the flow of oxygen by increasing the flow of oxygen when the electronic flow control valve is open.

7. The method of claim 6, wherein compensating further comprises:
    selecting a volumetric flow rate;
    calculating a volume of oxygen not delivered during the closing of the electronic flow control valve based on the volumetric flow rate, the predetermined time interval, and the predetermined time period;
    and wherein the method further comprises increasing the flow of oxygen when the electronic flow control valve is open to deliver the volume of oxygen not delivered during the closing of the electronic flow control valve.

8. A method of preventing a fire in an oxygen delivery device system, the method comprising:
    providing an oxygen delivery device, the oxygen delivery device comprising a controller in communication with an electronic flow control valve;
    delivering a flow of oxygen from a pressurized oxygen source to a patient interface through tubing, the electronic flow control valve in communication with the tubing to selectively stop the flow of oxygen through the tubing;
    at a predetermined time interval, the controller closing the electronic flow control valve to pause the flow of oxygen for a predetermined time period to remove oxygen that may serve as an oxidizer to a fire inside at least one of the patient interface and tubing; and
    compensating for a volume of oxygen not delivered during the closing of the electronic flow control valve to pause the flow of oxygen.

9. The method of claim 8, wherein the predetermined time interval is from about every 5 seconds to about every 60 seconds, and wherein the predetermined time period is from about 0.1 seconds to 1.5 seconds.

10. The method of claim 8, wherein the method further comprises delivering a pulse of high-flow oxygen after closing the electronic flow control valve to pause the flow of oxygen for the predetermined time period, the pulse of high-flow oxygen further extinguishing the fire when the fire is present in at least one of the patient interface and the tubing.

11. The method of claim 10, wherein the pulse of high-flow oxygen is delivered for about 100 to about 500 milliseconds, and wherein the pulse of high-flow oxygen has a flow rate of about 15 to about 30 liters per minute.

12. The method of claim 8, wherein compensating for the closing of the electronic flow control valve to pause the flow of oxygen comprises increasing the flow of oxygen when the electronic flow control valve is open.

13. The method of claim 12, wherein compensating for the closing of the electronic flow control valve to pause the flow of oxygen further comprises:
selecting a volumetric flow rate;
calculating the volume of oxygen not delivered during the closing of the electronic valve based on the volumetric flow rate, the predetermined time interval, and the predetermined time period;
and increasing the flow of oxygen when the electronic flow control valve is open to deliver the volume of oxygen not delivered during the closing of the electronic flow control valve.

14. A system for reducing a risk of fire in an oxygen delivery system, the system comprising:
an oxygen delivery device, the oxygen delivery device comprising a controller and a flow control valve to control a flow of oxygen through a tubing from an oxygen source to a patient interface; and
the controller in communication with the flow control valve, the controller programmed to close the flow control valve for a predetermined time period at a predetermined time interval to cause a periodic oxygen pause and control a flow rate of the flow of oxygen through the tubing from the oxygen source to the patient interface, the periodic oxygen pause to remove oxygen that may serve as an oxidizer for a fire inside at least one of the patient interface and the tubing, and
the predetermined time interval being from about every 5 seconds to about every 30 seconds and wherein the predetermined time period is from about 0.1 seconds to 1.5 seconds.

15. The system for reducing the risk of fire in an oxygen delivery system of claim 14, wherein the controller is further programmed to cause a pulse of high-flow oxygen after the periodic oxygen pause, the pulse of high-flow oxygen extinguishing the fire inside at least one of the patient interface and the tubing.

16. The system for reducing the risk of fire in an oxygen delivery system of claim 15, wherein the controller is programmed to cause the pulse of high-flow oxygen to be delivered for about 100 to about 500 milliseconds, and wherein the pulse of high-flow oxygen has a flow rate of about 15 to about 30 liters per minute.

17. The system for reducing the risk of fire in an oxygen delivery system of claim 15, wherein the controller is programmed to compensate for the periodic oxygen pause by increasing the flow of oxygen when the flow control valve is open.

18. The system for reducing the risk of fire in an oxygen delivery system of claim 17, wherein the controller is programmed to compensate for the periodic oxygen pause by:
calculating a volume of oxygen not delivered during the closing of the flow control valve based on a selected volumetric flow rate, the predetermined time interval, and the predetermined time period; and
increasing the flow of oxygen when the flow control valve is open to deliver the volume of oxygen not delivered during the closing of the flow control valve.

19. The system for reducing the risk of fire in an oxygen delivery system of claim 14, the system further comprising the patient interface, and wherein the patient interface is selected from one of a nasal cannula, a CPAP mask, an auxiliary oxygen tube, and a drug nebulizer.

20. The system for reducing the risk of fire in an oxygen delivery system of claim 19, wherein the patient interface includes a connector for connecting the patient interface to the oxygen delivery control device, and wherein the oxygen delivery device comprises a receptacle for receiving the connector of the patient interface.

21. A system for reducing a risk of fire in an oxygen delivery system, the system comprising:
an oxygen delivery device, the oxygen delivery device comprising a controller and a flow control valve to control a flow of oxygen through a tubing from an oxygen source to a patient interface; and
the controller in communication with the flow control valve, the controller programmed to close the flow control valve for a predetermined time period at a predetermined time interval to cause a periodic oxygen pause and control a flow rate of the flow of oxygen through the tubing from the oxygen source to the patient interface, the periodic oxygen pause to remove oxygen,
wherein the controller is programmed to compensate for the periodic oxygen pause by:
calculating a volume of oxygen not delivered during the closing of the flow control valve based on a selected volumetric flow rate, the predetermined time interval, and/or the predetermined time period; and
increasing the flow of oxygen when the flow control valve is open to deliver the volume of oxygen not delivered during the closing of the flow control valve.

* * * * *